US012558340B2

(12) United States Patent
Missling et al.

(10) Patent No.: US 12,558,340 B2
(45) Date of Patent: Feb. 24, 2026

(54) ANAVEX2-73 FOR THE TREATMENT OF GENETIC NEURODEVELOPMENTAL DISORDERS

(71) Applicant: ANAVEX LIFE SCIENCES CORP., New York, NY (US)

(72) Inventors: Christopher U. Missling, New York, NY (US); Alani Selvey, New York, NY (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 1034 days.

(21) Appl. No.: 17/581,794

(22) Filed: Jan. 21, 2022

(65) Prior Publication Data

US 2022/0142968 A1      May 12, 2022

Related U.S. Application Data

(63) Continuation-in-part of application No. PCT/US2020/043007, filed on Jul. 22, 2020.

(60) Provisional application No. 62/877,074, filed on Jul. 22, 2019.

(51) Int. Cl.
*A61K 31/341*        (2006.01)
*A61P 25/28*         (2006.01)

(52) U.S. Cl.
CPC ............ *A61K 31/341* (2013.01); *A61P 25/28* (2018.01)

(58) Field of Classification Search
CPC .... A61K 31/341; A61K 9/0053; A61K 47/10; A61K 47/12; A61K 47/26; A61K 47/36; A61K 9/0095; A61P 25/28; A61P 25/00
See application file for complete search history.

(56) References Cited

U.S. PATENT DOCUMENTS

| | | |
|---|---|---|
| 9,750,746 B2 | 9/2017 | Vamvakides et al. |
| 10,507,196 B2 | 12/2019 | Missling et al. |
| 10,888,543 B2 | 1/2021 | Missling |
| 11,446,275 B2 | 9/2022 | Missling |
| 11,839,600 B2 | 12/2023 | Missling |
| 2019/0022052 A1 | 1/2019 | Missling et al. |

FOREIGN PATENT DOCUMENTS

| | | | | |
|---|---|---|---|---|
| GR | 1008233 | B | 6/2014 | |
| WO | 1997030983 | A1 | 8/1997 | |
| WO | WO-2017132127 | A1 * | 8/2017 | .......... A61K 31/341 |
| WO | WO-2018022848 | A1 * | 2/2018 | .......... A61K 31/341 |

OTHER PUBLICATIONS

Rossignol, Annals of Clinical Psychiatry, 2009, vol. 21, No. 4 (Year: 2009).*
Dy, Pediatr. Neurol. 2017, 75:91-95 (Year: 2017).*
Reyes, Sci. Rep. 11, 17150, 2021 (Year: 2021).*
Zafarullah, Brain Sci. 2019, 9, 96 (Year: 2019).*
Anavex Life Sciences Corp., "ANAVEX2-73 Study in Patients With Rett Syndrome (AVATAR)," May 8, 2019, 8 pages, Retrieved from the Internet: URL:https://clinicaltrials.gov/ct2/show/NCT03941444 on Jul. 19, 2022.
Rebowe N., et al., "Anavex 2-73 as a Potential Treatment for Rett Syndrome and Other Pediatric or Infantile Disorders with Seizure Pathology," Jun. 22-24, 2016, pp. 1-30, Retrieved from the Internet: URL: https://s3.amazonaws.com/foxgl-sbfq/Rett%20and%20infantile%20Spasms%20AV2-73%20Presentation.pdf on Mar. 24, 2017.
Supplementary European Search Report for European Patent Application 20844208.7 dated Jul. 27, 2022, 2 Pages.
International Search Report and Written Opinion mailed Oct. 16, 2020 for International Patent Application No. PCTUS2020/043007.
Berry-Kravis E.M., et al., "Drug Development for Neurodevelopmental Disorders: Lessons Learned from Fragile Xsyndrome", Nature Reviews, 2018, vol. 17, pp. 280-298.
Busner J., et al., "The Clinical Global Impressions Scale," Applying a Research Tool in Clinical Practice, Psychiatry, 2007, pp. .29-37.
Communication Pursuant to Article 94(3) EPC for European Patent Application No. 20844208.7, mailed on Feb. 16, 2024, 7 pages.
Evers M., et al.,"The Role of Glutamate in Pathogenesis and Treatment," Chapter 6: Excitotoxicity in Austism , Humana Press, 2008, pp. 133-145.
Homberg J.R., et al., "Improving Treatment of Neurodevelopmental Disorders : Recommendations Based on Preclinical Studies," Expert Opinion on Drug Discovery, 2015, vol. 11, 16 pages.
Non-Final Office Action for U.S. Appl. No. 17/629,321, dated Apr. 17, 2025, 22 pages.

* cited by examiner

*Primary Examiner* — Jeffrey H Murray
*Assistant Examiner* — Luisalberto Gonzalez
(74) *Attorney, Agent, or Firm* — Polsinelli PC

(57) ABSTRACT

The present invention provides methods for treating a genetic neurodevelopmental disorder, such as Rett syndrome or Fragile X-syndrome, comprising evaluating a subject for his/her occurrence and/or severity of symptoms and/or specific biomarker levels before administering a dosage formulation of ANAVEX2-73 to the subject, administering the dosage formulation of ANAVEX2-73 to the subject for a period of time, re-evaluating the occurrence and/or severity of symptoms and/or specific biomarker levels, and optionally modifying the dosage of ANAVEX2-73 administered to the subject based on the re-evaluation results.

7 Claims, 12 Drawing Sheets

ANAVEX2-73 FOR THE TREATMENT OF GENETIC NEURODEVELOPMENTAL DISORDERS

CROSS-REFERENCE TO RELATED APPLICATION

This application claims benefit of and is a continuation-in-part application of PCT application No. PCT/US2020/043007 filed on Jul. 22, 2020, which in turn claims the benefit of U.S. Provisional Patent Application No. 62/877,074, which was filed in the U.S. Patent and Trademark Office on Jul. 22, 2019, both of which are incorporated herein by reference in their entirety for all purposes.

FIELD OF THE INVENTION

The present disclosure generally relates to methods for treating genetic neurodevelopmental disorders.

BACKGROUND OF THE INVENTION

Genetic neurodevelopmental disorders include disorders with severely affected behavioral features caused by alterations in early brain development. The various genetic neurodevelopmental disorders show many symptoms of brain dysfunction such as sensory and motor system difficulties, speech and language problems, and a variety of cognitive impairments (learning and organizational skills). These disorders can be classified in specific groups by their cause.

The first group, known as the Aneuploidy group, comprises disorders caused by an abnormal number of chromosomes. The primary example in this group is Down's syndrome.

The second group consists of disorders chromosomal micro-deletions, such as the deletion of a chromosomal region. Examples in this group are William's Beuren syndrome, Prader-Willi syndrome, Angelman syndrome, Smith-Magenis syndrome, and velo-cardio-facial syndrome.

The third group consists of disorders having a single gene defect. Examples in this group are ATR-X syndrome, Barth syndrome, Fragile X-syndrome, ICF syndrome, Neurofibromatosis, Rett syndrome, and Smith-Lemli-Opitz syndrome.

The last group is believed to be caused by a combination of genetic, environmental, and epigenetic factors. Examples in this group are addictive disorders, ADHD, anxiety disorders, Asperger's syndrome, autistic disorders, depression, dyslexia, eating disorders, epilepsy, infantile spasms, fetal alcohol syndrome, hydrocephalus, manic depressive illness, mental retardation, schizophrenia, spina bifida, and Tourette's syndrome.

A need remains for more effective therapies for treating genetic neurodevelopmental disorders that can address multiple symptoms, reduce the need to resort to multiple different drugs and other treatments, do not cause adverse events and are amenable to preparation as dosage formulations that are convenient for administering to children or cognitively or physically impaired individuals.

SUMMARY OF THE INVENTION

Figure 1:
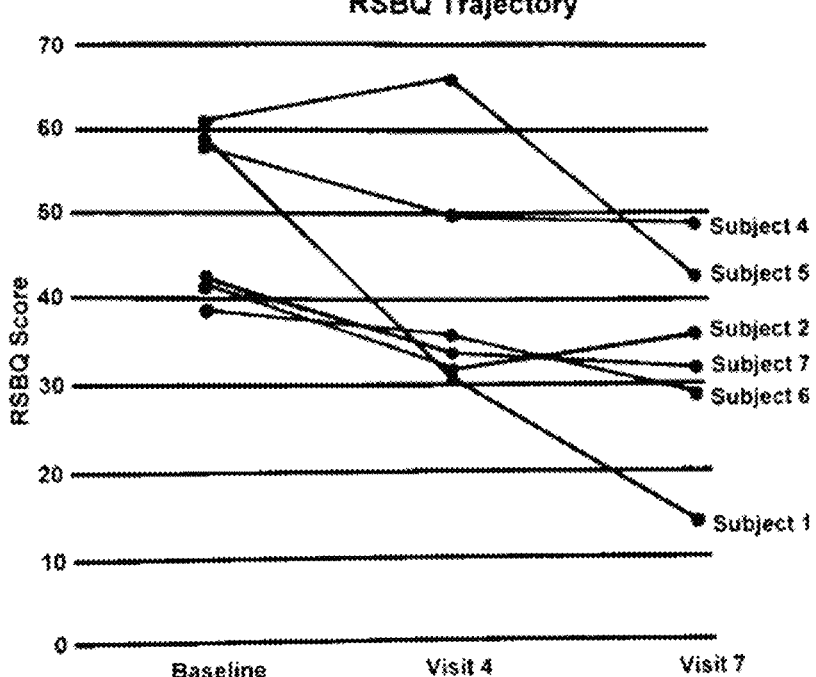
FIG. 1 is a graph of a behavioral index (RSBQ Total Score) over time in 6 young adult female Rett syndrome patients treated daily with 5 mg ANAVEX2-73 in a liquid formulation, from week 0 to end of treatment at Week 7.

Disclosed herein are methods and pharmaceutical compositions for treating a genetic neurodevelopmental disorder.

In one aspect, disclosed herein, is a method for treating a genetic neurodevelopmental disorder, the method comprising: (a) evaluating the patient for one or more symptoms selected from a group consisting of cognition, motor learning, balance, muscular strength, seizures, sleep habits, breathing problems, anxiety, and adverse events; (b) administering to a subject in need thereof a dosage formulation comprising a therapeutically effective amount of ANAVEX2-73; (c) evaluating the patient for an improvement or deterioration in one or more symptoms in (a); and (d) increasing or decreasing the dosage formulation of ANAVEX2-73 based on the evaluation in (c); wherein the dosage formulation is selected from a liquid oral dosage formulation, a topical formulation, a transmucosal formulation, a transdermal formulation, a buccal formulation, a sublingual formulation, and a parental formulation.

In another aspect, as disclosed herein, is a method for treating a genetic neurodevelopmental disorder, the method comprising: (a) evaluating the patient using Rett Syndrome Behavior Questionare (RSBQ), Clinical Global Impressions-Improvement (CGI-I), one or more symptoms consisting of consisting of cognition, hand behaviors, motor learning, balance, muscular strength, seizures, sleep habits, breathing problems, anxiety, adverse events, and measuring a biomarker, which comprises plasma glutamate, PI3K, Akt, mTOR, MAPK, ERK, or any combinations, in the subject to determine a baseline biomarker level; (b) administering to a subject in need thereof a dosage formulation comprising a therapeutically effective amount of ANAVEX2-73; (c) evaluating the patient for an improvement or deterioration in Rett Syndrome Behavior Questionare (RSBQ), Clinical Global Impressions-Improvement (CGI-I), one or more symptoms in (a), and the biomarker after about 1 week to determine a second biomarker level and comparing the second biomarker level to the baseline biomarker level; and (d) increasing or decreasing the dosage formulation of ANAVEX2-73 based on the evaluation in (c). For example, the occurrence of an adverse event indicates decreasing the dosage of ANAVEX2-73, and the second biomarker level about the same or higher than the baseline biomarker level indicates optionally increasing the dosage of ANAVEX2-73; wherein the dosage formulation is selected from a liquid oral dosage formulation, a topical formulation, a transmucosal formulation, a transdermal formulation, a buccal formulation, a sublingual formulation, and a parental formulation.

In another aspect, as disclosed herein, is a use of ANAVEX2-73 in the manufacture of a medicament for the treatment of a genetic neurodevelopmental disorder.

A therapeutically effective amount is an amount effective for alleviating symptoms of a genetic neurodevelopmental disorder selected from the group consisting of Down's syndrome, William's Beuren syndrome, Prader-Willi syndrome, Angelman syndrome, Smith-Magenis syndrome, velo-cardio-facial syndrome, ATR-X syndrome, Barth syndrome, Fragile X-syndrome, ICF syndrome, Neurofibromatosis, Rett syndrome, Smith-Lemli-Opitz syndrome, an addictive disorder, ADHD, an anxiety disorder, Asperger's syndrome, an autistic disorder, depression, dyslexia, an eating disorder, epilepsy, infantile spasms, fetal alcohol syndrome, hydrocephalus, manic depressive illness, mental retardation, schizophrenia, spina bifida, or Tourette's syndrome. In one aspect, the therapeutically effective amount is about 0.2 mg to about 55 mg, about 0.2 mg to about 40 mg, about 0.2 mg to about 20 mg, about 0.2 mg to about 10 mg, 0.2 mg to about 5 mg, or about 1 mg to 2 mg of ANAVEX2-73. In another aspect, the administration to the subject is systemic, and may be achieved by any route of administration or dosage formulation, although oral administration, topical administration, transmucosal administration, transdermal administration, buccal administration, sublingual administration and parental administration are emphasized, along with dosage formulations adapted for such administration. In another aspect, the dosage formulation comprises ANAVEX2-73 at a concentration of about 0.2 mg/ml to about 8 mg/ml and a pharmaceutically acceptable carrier. In yet another aspect, the therapeutically effective amount of ANAVEX2-73 is administered in at least one dose of the liquid dosage formulation, and at least once daily.

In one aspect, as disclosed herein, is a method for selecting a subject for a treatment for a genetic neurodevelopmental disorder in a subject in need thereof, the method comprising: (a) using a Rett Syndrome Behavior Questionnaire (RSBQ) or a Clinical Global Impressions-Improvement (CGI-I), evaluating in the subject the severity and/or frequency of one or more neurodevelopmental disorder symptoms selected from the group consisting of: cognitive impairment, motor learning impairment, balance impairment, muscular strength impairment, seizures, sleep dysfunction, breathing impairment, and anxiety; (b) measuring a baseline level of a biomarker in the subject to determine a baseline biomarker level, wherein the biomarker comprises plasma glutamate, P I3K, pAkt, mTOR, pMAPK, pERK, or any combinations thereof; (c) selecting the subject for treatment with a dosage formulation comprising a therapeutically effective amount of ANAVEX2-73 for daily administration for a period of at least about 1 week, if the baseline biomarker level is elevated compared to a control biomarker level; wherein the control biomarker level is the biomarker level in a healthy subject; and wherein the dosage formulation is selected from a liquid oral dosage formulation, a topical formulation, a transmucosal formulation, a transdermal formulation, a buccal formulation, a sublingual formulation, and a parental formulation.

In one aspect, the subject selection is for treating the subject having a genetic neurodevelopmental disorder selected from the group consisting of Down's syndrome, William's Beuren syndrome, Prader-Willi syndrome, Angelman syndrome, Smith-Magenis syndrome, velo-cardio-facial syndrome, ATR-X syndrome, Barth syndrome, Fragile X-syndrome, ICF syndrome, Neurofibromatosis, Rett syndrome, Smith-Lemli-Opitz syndrome, an addictive disorder, ADHD, an anxiety disorder, Asperger's syndrome, an autistic disorder, depression, dyslexia, an eating disorder, epilepsy, infantile spasms, fetal alcohol syndrome, hydrocephalus, manic depressive illness, mental retardation, schizophrenia, spina bifida, or Tourette's syndrome. a genetic neurodevelopmental disorder selected from the group consisting of Down's syndrome, William's Beuren syndrome, Prader-Willi syndrome, Angelman syndrome, Smith-Magenis syndrome, velo-cardio-facial syndrome, ATR-X syndrome, Barth syndrome, Fragile X-syndrome, ICF syndrome, Neurofibromatosis, Rett syndrome, Smith-Lemli-Opitz syndrome, an addictive disorder, ADHD, an anxiety disorder, Asperger's syndrome, an autistic disorder, depression, dyslexia, an eating disorder, epilepsy, infantile spasms, fetal alcohol syndrome, hydrocephalus, manic depressive illness, mental retardation, schizophrenia, spina bifida, or Tourette's syndrome.

Other features and iterations of the invention are described in more detail below.

DETAILED DESCRIPTION OF THE INVENTION

One aspect of the present disclosure provides a method for treating a genetic neurodevelopmental disorder, the method comprising: (a) evaluating, having evaluated or obtaining an evaluation of the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety; (b) daily administering to the subject a dosage formulation comprising a therapeutically effective amount of ANAVEX2-73 for a period of at least about 1 week, wherein the dosage formulation is selected from a liquid oral dosage formulation, a topical formulation, a transmucosal formulation, a transdermal formulation, a buccal formulation, a sublingual formulation, and a parental formulation; (c) re-evaluating, having re-evaluated or obtaining a re-evaluation the subject for the occurrence and/or severity of the symptoms evaluated in (a), and evaluating, having evaluated or obtaining an evaluation of the subject for the occurrence of adverse events; and (d) optionally modifying the dosage of ANAVEX2-73 administered to the subject based on the evaluations in (c), wherein absence of improvement in at least one symptom indicates optionally increasing the dosage of ANAVEX2-73, and occurrence of an adverse event indicates decreasing the dosage of ANAVEX2-73.

In another aspect, as disclosed herein, is a method for treating a genetic neurodevelopmental disorder, the method comprising: (a) evaluating the patient using Rett Syndrome Behavior Questionare (RSBQ), Clinical Global Impressions-Improvement (CGI-I), one or more symptoms consisting of consisting of cognition, hand behaviors, motor learning, balance, muscular strength, seizures, sleep habits, breathing problems, anxiety, adverse events, and/or measuring a biomarker, which comprises plasma glutamate, PI3K, Akt, mTOR, MAPK, ERK, or any combinations, in the subject to determine a baseline biomarker level; (b) administering to a subject in need thereof a dosage formulation comprising a therapeutically effective amount of ANAVEX2-73; (c) evaluating the patient for an improvement or deterioration in Rett Syndrome Behavior Questionare (RSBQ), Clinical Global Impressions-Improvement (CGI-I), one or more symptoms in (a), and the biomarker after about 1 week to determine a second biomarker level and comparing the second biomarker level to the baseline biomarker level; and (d) increasing or decreasing the dosage formulation of ANAVEX2-73 based on the evaluation in (c). For example, the occurrence of an adverse event indicates decreasing the dosage of ANAVEX2-73, and the second biomarker level about the same or higher than the baseline biomarker level indicates optionally increasing the dosage of ANAVEX2-73; wherein the dosage formulation is selected from a liquid oral dosage formulation, a topical formulation, a transmucosal formulation, a transdermal formulation, a buccal formulation, a sublingual formulation, and a parental formulation.

In another aspect of the present disclosure encompasses the use of ANAVEX2-73 in the manufacture of a medicament for the treatment of genetic neurodevelopmental disorders. In various aspects, the dosage formulation or medicament may be formulated as detailed further below, for example as formulations intended for oral administration, topical administration, transmucosal administration, sublingual administration, buccal administration, transdermal administration, and parental administration. Dosage formulations include, for example, liquid dosage formulations for parenteral or oral administration, and thin film formulations for oral or buccal administration or as a patch for transdermal administration.

Another aspect of the present disclosure provides a method for treating a genetic neurodevelopmental disorder, the method comprising: (a) evaluating, having evaluated or obtaining an evaluation of the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety; (b) measuring or obtaining a measurement of a baseline plasma glutamate level in the subject; (c) daily administering to the subject a dosage formulation comprising a therapeutically effective amount of ANAVEX2-73 for a period of at least about 1 week, wherein the dosage formulation is selected from a liquid oral dosage formulation, topical administration, transmucosal administration, transdermal administration, buccal administration, sublingual administration, and parental formulations; (d) re-evaluating, having re-evaluated or obtaining a re-evaluation of the subject for the occurrence and/or severity of the symptoms evaluated in (a), evaluating, having evaluated or obtaining an evaluation of the subject for the occurrence of adverse events; and measuring or obtaining a measurement of the level of plasma glutamate in the subject to determine a second glutamate level and comparing the second glutamate level to the baseline glutamate level; and (e) optionally modifying the dosage of ANAVEX2-73 administered to the subject based on the evaluations and glutamate level in (d), wherein absence of improvement in at least one symptom indicates optionally increasing the dosage of ANAVEX2-73, occurrence of an adverse event indicates decreasing the dosage of ANAVEX2-73, and a second glutamate level about the same or higher than the baseline glutamate level indicates optionally increasing the dosage of ANAVEX2-73.

In one aspect, as disclosed herein, is a method for selecting a subject for a treatment for a genetic neurodevelopmental disorder in a subject in need thereof, the method comprising: (a) using a Rett Syndrome Behavior Questionnaire (RSBQ) or a Clinical Global Impressions-Improvement (CGI-I), evaluating in the subject the severity and/or frequency of one or more neurodevelopmental disorder symptoms selected from the group consisting of: cognitive impairment, motor learning impairment, balance impairment, muscular strength impairment, seizures, sleep dysfunction, breathing impairment, and anxiety; (b) measuring a baseline level of a biomarker in the subject to determine a baseline biomarker level, wherein the biomarker comprises plasma glutamate, P I3K, pAkt, mTOR, pMAPK, pERK, or any combinations thereof; (c) selecting the subject for treatment with a dosage formulation comprising a therapeutically effective amount of ANAVEX2-73 for daily administration for a period of at least about 1 week, if the baseline biomarker level is elevated compared to a control biomarker level; wherein the control biomarker level is the biomarker level in a healthy subject; and wherein the dosage formulation is selected from a liquid oral dosage formulation, a topical formulation, a transmucosal formulation, a transdermal formulation, a buccal formulation, a sublingual formulation, and a parental formulation.

In still another aspect, the present disclosure encompasses the use of ANAVEX2-73 in the treatment of a genetic neurodevelopmental disorder, such as but not limited to Rett syndrome or Fragile X-syndrome.

(I) Formulations Comprising ANAVEX2-73

Dosage formulations used in the disclosed methods comprise a therapeutically effective amount of ANAVEX2-73, the crystalline HCI salt of tetrahydro-N,N-dimethyl-2,2-diphenyl-3-furanmethanamine, or tetrahydro-N,N-dimethyl-2,2-diphenyl-3-furanmethanamine hydrochloride (IUPAC name: 1-(2,2-diphenyloxolan-3-yl)-A/,A/-dimethylmethanamine hydrochloride). ANAVEX2-73 surprisingly combines the properties of low molecular weight, excellent chemical stability and high water solubility. Further, the free base form of ANAVEX2-73 is surprisingly soluble in almost all organic solvents, from alcohols such as propanol and butanol to acetone and hexane. Thus ANAVEX2-73 (used herein to refer to the HCI salt or the free base) is highly amenable to incorporation in the dosage formulations disclosed herein. For example, ANAVEX2-73 as either the HCI salt or the free base has a relatively low molecular weight (<400 Da), and is thus well suited for transmucosal or transdermal delivery, or rapid oral delivery. ANAVEX2-73 has a pKa around 8-9, which also makes it well-suited for transmucosal delivery. Therapeutically effective doses of ANAVEX2-73 are well suited for various thin film formulations, including oral and transdermal thin film formulations.

A dosage formulation or medicament as disclosed herein further comprises at least one pharmaceutically acceptable excipient. Non-limiting examples of pharmaceutically acceptable excipients are an aqueous carrier, an organic carrier, an inorganic carrier, preservatives, stabilizers, wetting agents, emulsifiers, buffers, coloring agents, flavoring agents, vitamins, or combinations thereof. These excipients do not deleteriously react with the ANAVEX2-73.

A therapeutically effective amount of ANAVEX2-73 can and will vary depending on the age of the subject, the weight of the subject, and the severity of the genetic neurodevelopmental disorder. A therapeutically effective amount of ANAVEX2-73 may range from about 0.2 mg to about 55 mg. In various aspects, a therapeutically effective amount of ANAVEX2-73 may range from about 0.2 mg to about 55 mg, from about 1 mg to about 30 mg, from about 1 mg to about 20 mg, from about 1 mg to about 10 mg, or from about 1 mg to about 5 mg. The maximum therapeutic dose of ANAVEX2-73 is about 55 mg.

Generally, a therapeutic amount of ANAVEX2-73 in a liquid dosage formulation may comprise a concentration of ANAVEX2-73 from about 0.1 mg/mL or about 0.2 mg/mL to about 0.5, 0.7. 0.80.9, 1, 2, 3, 4, 5, 6, 8, 10, 15, 20, 25, 30, 35, 40, 45, 50 or 55 mg/mL. In various aspects, the concentration of the liquid dosage formulation may be from about 0.1 mg/mL to about 8 mg/mL, about 1 mg/mL to about 6 mg/mL, or about 2 mg/mL to about 4 mg/ml. By way of non-limiting example, a subject in need thereof may be administered 5 mL of a 0.2 mg/mL liquid formulation. This dosage provides a therapeutically effective amount of ANAVEX2-73 of 1 mg. In another non-limiting example, a subject in need thereof may be administered 5 mL of an 8 mg/mL liquid formulation. This dosage provides a therapeutically effective amount of ANAVEX2-73 of 40 mg. In another non-limiting example, a subject in need thereof may be administered 1 mL of a 5 mg/mL liquid formulation. This dosage provides a therapeutically effective amount of ANAVEX2-73 of 5 mg. By way of further non-limiting examples, a daily dose of ANAVEX2-73 in a liquid formulation may be about 0.5 mg, about 1 mg, about 2 mg, about 3 mg, about 4 mg, about 5 mg, about 6 mg, about 7 m, about 8 mg, about 9 mg or about 10 mg.

Depending on the therapeutically effective amount to be dosed to the subject, the amount of ANAVEX2-73 contained in the dosage formulation, and the type of dosage formulation and route of administration, an appropriate volume or amount of the dosage formulation is obtained to deliver the therapeutically effective amount of ANAVEX2-73 to the subject. For example, the specific volume of a liquid oral dosage formulation having a certain concentration of ANAVEX2-73 may be measured by a number of known measuring devices, such as a syringe.

A carrier may be aqueous, organic, inorganic, or any combination thereof. Non-limiting examples of a carrier are water, polyethylene glycol, propylene glycol, ethanol, corn oil, cottonseed oil, peanut oil, sesame oil, benzyl alcohol, protein carriers, lipids, aqueous sodium chloride, agar, agaropectin, xanthan gum, guar gum, liposomes, niosomes, transferosomes, glycerin, and/or various buffers. In one aspect, a combination of water and glycerin is used as the carrier. Generally, the volume ratio of water to glycerin may range from about 1:3 to 3:1. In various aspects, the volume ratio of water to glycerin may range from about 1:3, from about 1:1, or from about 3:1.

In one aspect, an excipient may be a diluent. A diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated (phosphorylated) corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another aspect, an excipient may be a binder. Suitable binders include, but are not limited to starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinyl-alcohols, C12-C18 fatty acid alcohol, polyethylene glycol, polyols, saccharides, oligosaccharides, polypeptides, oligopeptides, and combinations thereof.

In another aspect, an excipient may be a filler. Suitable fillers include, but are not limited to carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another aspect, an excipient may be a buffering agent. Representative examples of suitable buffering agents include, but are not limited to phosphates, carbonates, citrates, tris buffers, and buffered saline salts (e.g., Tris buffered saline or phosphate buffered saline).

In various aspects, an excipient may be a pH modifier, to adjust pH of the formulation to a desired level. As will be appreciated, the pH of the liquid dosage formulation can have an impact on the taste and stability of the liquid dosage formulation. Basic liquid formulations do not exhibit improved taste, while acidic liquid formulations do exhibit improved taste. Additionally, in any formulation containing one or more preservatives, pH can have an impact on efficacy of the preservative(s). By way of non-limiting example, the pH modifying agent may be sodium carbonate, sodium bicarbonate, sodium citrate, citric acid, trisodium citrate, or phosphoric acid. In general, the pH of the formulation considering the stability of ANAVEX2-73 may be either basic or acidic. For example, the liquid dosage formulation may be acidic, generally in the range of about pH 3.0 to about 6.5. In various examples, the pH of the oral dosage formulation is about 4.2, about 4.6, or about 6.0. In another aspect, the formulations disclosed herein encompass any formulation containing sodium benzoate as a preservative, optionally in addition to a formulation containing a buffer system such as citrate/citric acid, and the pH is adjusted to about pH 3.0 to about 5, or to about 4.2, or about 4.6.

In a further aspect, an excipient may be a disintegrant. The disintegrant may be non-effervescent or effervescent. Suitable examples of non-effervescent disintegrants include, but are not limited to starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another aspect, an excipient may be a dispersant or dispersing enhancing agent. Suitable dispersants include, but are not limited to starch, alginic acid, polyvinylpyrrolidones, guar gum, kaolin, bentonite, purified wood cellulose, sodium starch glycolate, isoamorphous silicate, and microcrystalline cellulose.

In still another aspect, an excipient may be a preservative. Non-limiting examples of suitable preservatives include antioxidants, such as BHA, BHT, vitamin A, vitamin C, vitamin E, or retinyl palmitate, sodium benzoate, trisodium citrate, citric acid, sodium citrate; chelators such as EDTA or EGTA; and antimicrobials, such as parabens, chlorobutanol, or phenol. The preservative in the liquid dosage formulation is citric acid, sodium citrate, sodium benzoate, or combinations thereof.

In a further aspect, an excipient may be a lubricant. Non-limiting examples of suitable lubricants include minerals such as talc or silica; and fats such as vegetable stearin, magnesium stearate or stearic acid.

In another aspect, an excipient may be a sweetening agent. Non-limiting examples of sweetening agent may especially suited for, though not limited to, treatment of children for neurodevelopment disorders such as Rett syndrome. Non-limiting exemplary flavors are orange, lemon, lime, lemon-lime, lemonade, cherry (including sour cherry and black cherry), passion fruit, strawberry, blueberry, raspberry, mixed berry, and grape. In general, the concentration of the flavoring agent in the formulation may range from about 0.5% to about 1.0%. In various aspects, the concentration of the flavoring agent may range from about 0.1% to about 1.0%, from about 0.25% to about 0.75%, or from about 0.4% to about 0.6%. In one aspect, the concentration of the flavoring agent is about 0.5%. In another aspect, a bitterness masking agent is a commercially available bitterness masking agent, used to mask or block bitter taste of other formulation components. One such bitterness masking agent is a natural masking agent powder (29250) available from Flavor Chem Corporation (Downer's Grove, IL).

In another aspect, an excipient may be a thickening agent. Non-limiting examples of these components are xantham gum, guar gum, poloxamer, pectin, agar, gelatin, salts of alginic acid, carrageenan locust bean gum, and any combination thereof. By way of non-limiting example, a thickening agent is xantham gum.

In still a further aspect, an excipient may be a coloring agent. Suitable color additives include, but are not limited to, food, drug and cosmetic colors (FD&C), drug and cosmetic colors (D&C), or external drug and cosmetic colors (Ext. D&C).

Non-limiting examples of suitable liquid formulations comprising ANAVEX2-73 for treating genetic neurodevelopmental disorders are shown in Table 1

TABLE 1

| | Liquid Formulations of ANAVEX2-73 for Oral Administration | | | | |
|---|---|---|---|---|---|
| Component | Form 1 (wt %) | Form 2 (wt %) | Form 3 (wt %) | Form 4 (wt %) | Form 5 (wt %) |
| ANAVEX2-73 | 0.4 | 0.9 | 1.0 | 1.0 | 0.5 |
| Xanthan gum | 0.9 | 0.9 | 0 | 0 | 0 |
| Glycerin | 43.8 | 43.8 | 25 | 50.0 | 50.0 |
| Sucralose/Flavoring agent | 0.5 | 0.5 | 0.4 | 1.4 | 0.8 |
| Citric acid (anhydrous) | 0.9 | 0.9 | 0 | 1.2 | 0.6 |
| Sodium citrate, dihydrate | 1.4 | 1.4 | 0 | 0 | 0 |
| Sodium Benzoate | 0.2 | 0.2 | 0 | 0 | 0 |
| Poloxamer 188 | 0 | 0 | 0 | 0 | 0.1 |
| Water | Q.s to 100.00% | Q.s to 100.00% | Q.s to 100.00% | Q.s to 100.00% | Q.s to 100.00% | sucralose, saccharin, aspartame, mannitol, sorbitol, sucrose, maltose, fructose, lactose, xylitol, or combinations thereof. In one aspect, the sweetening agent is sucralose.

In yet another aspect, an excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; citric acid; and combinations thereof.

In an alternate aspect, an excipient may be a flavoring agent or bitterness masking agent. A flavoring agent may be chosen from synthetic flavor oils and flavoring aromatics and/or natural oils, extracts from plants, leaves, flowers, fruits, maltodextrin, hydroxypropyl, and combinations thereof. In one aspect, a flavoring agent is one that appeals to children, such as a fruit flavor. Dosage formulations prepared with children's' taste preferences in mind are A dosage formulation comprising a therapeutic amount of ANAVEX2-73 may be formulated for administration to a subject in need thereof by any of various administration routes. Non-limiting methods of administration are oral, topical, transmucosal, transdermal, buccal, sublingual, and parental.

In one aspect, the dosage formulation is a liquid formulation comprising a therapeutically effective amount ANAVEX2-73, a pharmaceutically acceptable carrier, a preservative, and a flavoring agent. Non-limiting examples of oral liquid dosage formulations are liquids, suspensions, syrups, and emulsions.

In another aspect, a dosage formulation comprising a therapeutically effective amount of ANAVEX2-73 comprises a film (e.g., a thin film) or a patch in a format configured for buccal, sublingual, oral, transmucosal, topical, transdermal or oral delivery of the ANAVEX2-73. Non-limiting examples of films are an oral film, a sublingual film, a buccal film, a transmucosal film, a topical patch, a buccal patch, or a transdermal patch. For example, ANAVEX2-73 may be incorporated into any of a number of films commercially available from tesa Labtec GmbH (Langenfeld, Germany): Transfilm®, Rapidfilm® and Mucofilm®. Transfilm® is a patch for administration in topical, buccal, and transdermal patches. In another example, ANAVEX2-73 may be incorporated into in Rapidfilm®. Rapidfilm® is an oral dosage film for rapid release of ANAVEX2-73 9. In an additional example, ANAVEX2-73 may be incorporated into Mucofilm®. Mucofilm® is a film for release of ANAVEX2-73 for sublingual administration and buccal administration, i.e., transmucosal administration. Each of these films comprises a therapeutically effective amount of ANAVEX2-73, at least one pharmaceutically acceptable carrier, at least one pharmaceutically acceptable excipient, and a preservative. In one aspect, a thin film formulation is adapted for application once monthly, once every other month, or once every 90 days. For example, a thin film topical or transdermal patch may be adapted for application once monthly, once every other month, or once every 90 days.

In another aspect, a dosage formulation comprising ANAVEX2-73 comprises drug particles of ANAVEX2-73 enclosed in a shell having controlled solubility. Upon parenteral administration such a drug formulation, a period of time elapses before the shell dissolves in the body, and thus releases the drug. Accordingly, ANAVEX2-73 can be prepared in dosage formulation configured for parenteral administration to allow for sustained or extended time release of the therapeutically effective amount of ANAVEX2-73 to the subject. For example, particles of ANAVEX2-73 can be coated with thin films of inorganic oxides forming coated microparticles.

These coated microparticles are suspended in a carrier and are administered parenterally. For example, particles of ANAVEX2-73 may be prepared by coating drug particles with PharmaShell® by Nanexa AB (Uppsala, Sweden), i.e., ANAVEX2-73 can be coated with zinc oxide, with the coating thickness controlling release rate of the ANAVEX2-73. By controlling the thickness of the shell with high precision, the rate of release of the drug can be accurately predicted, and a drug formulation for parenteral administration prepared which will last for weeks or months. A particulate drug formulation of ANAVEX2-73 such as one using a PharmaShell® coating can be adapted for once a day, once a week, twice a month, once monthly, once every other month or once every three months dosing of ANAVEX2-73. Less frequent dosing such as no more frequent than twice a month, or once a month dosing is highly desirable for any of the multiple indications as disclosed herein, and is emphasized for subjects suffering from Rett syndrome. These dosage formulations comprise, for example, a therapeutically effective amount of ANAVEX2-73, a coating comprising an inorganic oxide, at least one carrier, at least one pharmaceutically acceptable excipient, and a preservative.

(II) Methods for Treating Genetic Neurodevelopmental Disorders

Another aspect of the disclosure provides methods for treating genetic neurodevelopmental disorders. The methods comprise evaluating the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety. Use Fragile X syndrome (FXS) as an example. Also known as Martin- Bell syndrome, it is an inherited condition that causes developmental delays, intellectual disabilities, learning and behavioral issues, physical abnormalities, anxiety, attention-deficit/hyperactivity disorder and/or autism spectrum disorder, among other problems. It's the most common form of inherited intellectual and developmental disability (IDD). It gets the name because, when looked at through a microscope, part of the X chromosome looks "broken" or "fragile." FXS is one of three syndromes in the fragile X family. The other two syndromes are Fragile X-associated tremor/ataxia syndrome (FXTAS). Symptoms include balance problems, shaky hands, unstable mood, memory loss, cognitive problems and numbness in the hands and feet. Fragile X-associated primary ovarian insufficiency (FXPOI). Symptoms include reduced fertility, infertility, missing or unpredictable menstrual periods and premature menopause. It is caused by causes mild to severe intellectual disability. FXS affects both males and females, but females usually have milder symptoms. Symptoms include delays in talking, anxiety, and hyperactive behavior. Some people have seizures. Physical features might include large ears, a long face, a prominent jaw and forehead, and flat feet. Therapy can be used to treat learning disabilities. Medications may be used to treat anxiety and mood disorders. This evaluation may be performed by one or more healthcare professionals according to evaluation clinical methods described herein or any known clinical evaluation method.

In one aspect, the method further comprises measuring, or having measured or obtained a baseline biomarker level in the subject prior to treatment with ANAVEX2-73 as described herein, wherein the biomarker comprises plasma glutamate, gamma aminobutyric acid (GABA), PI3K, pAkt, mTOR, pMAPK, pERK, or any combinations thereof, and measuring or having measured or obtained at least a second level of the biomarker following a period of treatment with ANAVEX2-73 as described herein. Measurement of the biomarker level comprises withdrawing a whole blood sample from the subject, separating the blood plasma from remaining whole blood components such as by centrifuging the sample, isolating the blood plasma, and measuring the amount of biomarker, including but not limited to, glutamate, gamma aminobutyric acid (GABA), P I3K, pAkt, mTOR, pMAPK, and/or pERK in the blood plasma using any one of several techniques known in the art. Non-limiting examples of suitable techniques are high pressure liquid chromatography (HPLC), ELISA (enzyme-linked immunosorbent assay), gas chromatography-mass spectrometry (GCMS), or other methods known in the art. Such measurements may be performed by one or more technicians or healthcare professionals.

The methods may further comprise utilizing the Rett Syndrome Behavior Questionnaire (RSBQ) and/or a Clinical Global Impressions-Improvement (CGI-I) to evaluate the subject for the occurrence and/or severity of one or more genetic neurodevelopmental disorder symptoms, or having the subject evaluated or obtaining such an evaluation. The Rett Syndrome Behavior Questionnaire (RSBQ) and/or a Clinical Global Impressions-Improvement (CGI-I) can be completed by a custodian, parent, caregiver, or one or more healthcare professionals. The RSBQ and/or CGI-I has been shown to provide additional insight on the occurrence and/or severity of one or more genetic neurodevelopmental disorder symptoms in a subject. The methods may comprise utilizing Clinical Questionnaire for Fragile X Syndrome, together with the symptom evaluation as outlined above.

Using the above evaluation(s), one or more healthcare professionals will determine the therapeutic amount of ANAVEX2-73 to be administered to the subject. Routes of administration and formulations of ANAVEX2-73 are described in more detail above. It will be understood however that certain dosage formulations, such as flavored liquid oral dosage formulations and topical or transdermal thin film patches are especially useful in promoting patient compliance with a prescribed dosing regimen.

A dosage formulation of ANAVEX2-73 as disclosed herein is administered regularly for a period of at least several days or a week. As will be understood, depending on the dosage formulation regular administration may be once every other day, once daily, twice daily, or more than twice daily, or alternatively less frequently than once every other day, such as twice a week, once a week, bi-weekly (every two weeks), once a month, every two months, or once every three months. It will be understood that certain types of dosage formulations contemplated herein are well-adapted to less frequent than once daily administration, such as a thin film topical, or transdermal patch which may be adapted for application once monthly, once every other month, or once every 90 days; or a sustained or extended release microparticle formulation adapted for once a week, twice a month, once a month, once every other month or once every three months administration. The period of time during which the dosage formulation comprising a therapeutically effective amount of ANAVEX2-73 is administered can and will vary depending on a number of factors, including the severity of disorder being treated, the type of formulation, route and frequency of administration, the age of the subject, etc. Generally, the period of administration is at least several days or a week.

In various aspects, the period of administration is at least about 1 week, at least about 2 weeks, at least about 3 weeks, at least about 30 days, at least about 2 months, at least about 3 months, at least about 6 months, or at least about 1 year, but may be extended for longer than 1 year.

The methods disclosed herein can be used to treat a genetic neurodevelopmental disorder such as, but not limited to Down's syndrome, William's Beuren syndrome, Prader-Willi syndrome, Angelman syndrome, Smith-Magenis syndrome, velo-cardio-facial syndrome, ATR-X syndrome, Barth syndrome, Fragile X-syndrome, ICF syndrome, Neurofibromatosis, Rett syndrome, Smith-Lemli-Opitz syndrome, an addictive disorder, ADFID, an anxiety disorder, Asperger's syndrome, an autistic disorder, depression, dyslexia, an eating disorder, epilepsy, infantile spasms, fetal alcohol syndrome, hydrocephalus, manic depressive illness, mental retardation, schizophrenia, spina bifida, or Tourette's syndrome. In an exemplary aspect, the methods are used to treat Rett syndrome or Fragile X Syndrome.

The method further comprising re-evaluating the subject after the administration of ANAVEX2-73. This re-evaluation examines the occurrence and/or severity for symptoms, the occurrence of adverse events, the measurement of a second biomarker level, which includes but not limited to, plasma glutamate level, gamma aminobutyric acid (GABA) level, PI3K, pAkt, mTOR, pMAPK, and/or pERK levels, and comparing the second biomarker levels to the baseline biomarker levels, and the data obtained from the Rett Syndrome Behavior Questionnaire (RSBQ), and/or a Clinical Global Impressions-Improvement (CGI-I) and/or Clinical Questionnaire for Fragile X Syndrome. This re-evaluation may occur on a weekly, bi-weekly, or monthly basis.

The subject may show an improvement in one or more symptoms of the genetic neurodevelopmental disorder. Non-limiting examples of these symptoms are an improvement in muscular coordination, improvement in cognition, improvement in communication skills, reduction in hand movements, improvement in unusual eye movements, improvement in motor learning, improvement in balance, improvement in muscular strength, reduction in seizures, improvement in sleep habits, improvement in breathing problems, and reduction in anxiety. It will be understood that all such symptoms are readily assessed using clinical measures and evaluations commonly accessible and used by those of routine skill in the art.

One useful measure of improvement for one or more symptoms of a genetic neurodevelopmental disorder is a behavioral questionnaire that interrogates a primary caregiver of a subject at multiple time points during a course of treatment, regarding multiple behavioral indicators of the disorder. For example, a Rett Syndrome Behavior Questionnaire (RSBQ) may comprise multiple, e.g., at least five but optionally 10 or more, such as 12, 15, 20, 25, 30, 35, 40, 45 or 50 or more behavioral indicators which ask for a caregiver's observations of the subject regarding the frequency of specific episodes or occurrences of each indicator. For example, an RSBQ as used in Example 5 comprised 45 behavioral indicators which include the caregiver's assessment of the frequency of multiple behavioral indicators associated with Rett syndrome, such as (but not limited to) gesturing to obtain specific objects, hyperventilation, repetitive hand movements, spells of screaming, grinding teeth, abrupt change in mood, spells of anxiety/fear in unfamiliar situations, abrupt mood changes, uses eye gaze to convey feeling, needs, or wishes, vocalizes for no apparent reason, spells of panic, rocks body repeatedly, teeth grinding, and so on, or combinations thereof. On such a questionnaire, a caregiver's responses at each time point are standardized through the presentation of multiple choice options, for example the caregiver instructed to respond to indicate whether a given behavioral indicator is "very true or often true," or "somewhat or sometimes true," or "rarely true or not true." It should be understood that such questionnaires may be variously configured in terms of multiple choice options and number and selection of behavioral indicators, to arrive at results useful for assessing the therapeutic effect of treatment with ANAVEX2-73 in a liquid formulation.

Another useful measurement for one or more symptoms of a genetic neurodevelopmental disorder is a Clinical Global Impression-Improvement scale (CGI-I). This scale measures the improvement or worsening of the subject's condition relative to a baseline state before administration of the dosage form comprising a therapeutically acceptable amount of ANAVEX2-73, as assessed by one or more healthcare professionals. Another useful measurement for one or more symptoms of a genetic neurodevelopmental disorder is a Clinical Questionnaire for Fragile X Syndrome, or any other diagnostic or evaluation questionnaires.

Another useful measurement in the re-evaluation is the biomarker levels, such as plasma glutamate, gamma aminobutyric acid (GABA) level, PI3K, pAkt, mTOR, pMAPK, and/or pERK levels. Generally, a decrease in biomarker levels, such as plasma glutamate levels as compared to the baseline glutamate levels shows an improvement in the subject's condition. Conversely, an increase in the biomarker levels, such as plasma glutamate levels or pERK levels as compared to the baseline levels shows a worsening in the subject's condition.

One or more healthcare professionals optionally can modify the dosage amount of ANAVEX2-73 depending on the results of the re-evaluation. If the one or more healthcare professionals determine that improvements from the re-evaluation are seen, the one or more medical caregivers or healthcare professionals may maintain the dosage amount of ANAVEX2-73 or reduce the dosage amount of ANAVEX2-73. If the one or more healthcare professionals determine that absence of improvements from the re-evaluation are seen, the one or more healthcare professionals may increase the dosage amount or dose frequency of ANAVEX2-73.

The clinical safety of ANAVEX2-73 has been demonstrated in a randomized, placebo-controlled single ascending dose Phase 1 study of ANAVEX2-73 in 22 healthy male volunteers. (A Phase 1 Dose Escalation Study to Investigate Safety, Tolerability, and Pharmacokinetics of ANAVEX2-73 in Healthy Male Subjects, CNS Summit 2014, Boca Raton, Fla., by Ole Voges, Ingo Weigmann, Norman Bitterlich, Christoph Schindler and Christopher Missling). Ascending single oral doses of 1 mg, 10 mg, 30 mg, 40 mg, 50 mg, and 55 mg of ANAVEX2-73 were safe and well tolerated in healthy subjects. No serious adverse events occurred. Based on the frequency and intensity of non-treatment emergent adverse events (TEAEs) the maximum tolerable dose (MTD) and the minimum intolerable dose (MID) were defined as 55 mg and 60 mg, respectively. At highest doses, observed adverse events included only moderate and reversible dizziness and headache, common in drugs that target the central nervous system.

A formulation as disclosed herein is administered regularly for a period of at least several days or a week. Regular administration may be once every other day, once daily, twice daily, or more than twice daily, or alternatively less frequently than once every other day, such as twice a week, once a week, bi-weekly (every two weeks), once a month, every two months, or once every three months. It will be understood that certain types of dosage formulations contemplated herein are well-adapted to less frequent than once daily administration, such as a thin film topical, or transdermal patch which may be adapted for application once monthly, once every other month, or once every 90 days; or a sustained or extended release microparticle formulation adapted for once a month, once every other month or once every three months administration. The period of time during which the dosage formulation comprising a therapeutically effective amount of ANAVEX2-73 is administered can and will vary depending on a number of factors, including the severity of disorder being treated, the type of formulation, route and frequency of administration, the age of the subject, etc. Generally, the period of administration is at least several days or a week. In various aspects, the period of administration is at least about 30 days, at least about 2 months, at least about 3 months, at least about 6 months, or at least about 1 year, but may be extended for longer than 1 year.

During the period of administration, the therapeutic amount of ANAVEX2-73 in a dosage formulation may be increased or decreased by a concentration of ANAVEX2-73 in the formulation, depending on whether the subject shows an improvement in symptoms, a desirable change in biomarker levels, or any signs of adverse effects. Alternatively, the dosing frequency may be increased or decreased for the same reason using the same dosage formulation. Keep in mind, the approach is personalized for each patient, and should be applied with flexibility in consideration of patient's individual physical and mental conditions.

a. Definitions

When introducing elements of the various aspects described herein, the articles "a", "an", "the" and "said" are intended to mean that there are one or more of the elements. The terms "comprising", "including" and "having" are intended to be inclusive and mean that there may be additional elements other than the listed elements.

The phrase "therapeutically effective amount" refers to an amount effective, at dosages and for periods of time necessary, to achieve the desired therapeutic result with respect to genetic neurodevelopmental disorders. A therapeutically effective amount of AVANEX2-73 may be determined by a person skilled in the art and may vary according to factors such as the clinical state, age, and weight of the subject. A therapeutically effective amount is also one in which any toxic or detrimental effects of the active agent are outweighed by the therapeutically beneficial effects. A therapeutically effective amount also encompasses an amount that is effective, at dosages and for periods of time necessary, to achieve the desired results.

Having described the invention in detail, it will be apparent that modifications and variations are possible without departing from the scope of the invention defined in the appended claims.

EXAMPLES

The following examples illustrate various aspects of the invention.

Example 1: ANAVEX2-73 for Rett Syndrome

A female subject diagnosed with Rett Syndrome was administered 5 mL of a liquid formulation (0.2 mg/mL). The subjected after administration showed an improvement in motor skills and cognition.

Example 2: Dosage Formulations with ANAVEX2-73

Three dosage formulations were prepared with the following ingredients: sucralose, ANAVEX2-73 (salt form, 1 weight %), xantham gum, glycerin, flavoring agent, and water, each within the disclosed amount range for each component. Various combinations of sodium citrate, sodium benzoate, and citric acid were used to adjust the pH of the formulations. The first formulation was maintained at a pH of 4.2. The second formulation was maintained at a pH of 4.7. The third was maintained at a pH of 6.0

Example 3: Antimicrobial Testing

The first and third liquid dosage formulations described in Example 2 exhibit anti-microbial effectiveness (Antimicrobial Effectiveness Test, USP <51>). These formulations were inoculated with *Pseudomonas aeruginosa, Escherichia coli, Staphylococcus aureus, Candia albicans*, and *Aspergillus bradsiliensis*. In these tests, the inoculated formulations were at 40° C., 75% RH for 14 days. After 14 days, the formulation did not show significant microbial reduction or significant microbial growth. Elongated testing over a 3 month period did not show significant microbial reduction or significant microbial growth.

Example 4: Stability Tests

The second liquid dosage formulation, as described in Example 2, showed improved stability when measured at 25° C., 60% RH, and 40° C., 75% RH for at least 3 months. These stability tests measured the assay of ANAVEX2-73, pH, palatability, and antimicrobial effectiveness. After 3 months, the assay of ANAVEX2-73 was maintained.

Example 5: ANAVEX2-73 for Rett Syndrome

Six female subjects ranging from 16 to 22 years of age diagnosed with Rett Syndrome were administered 5 mg ANAVEX2-73 liquid formulation (1 m_of a 5 mg/ml_A-NAVEX2-73 solution) daily for a total daily dose of 1 mg, over a period of 7 weeks.

Prior to treatment, the subjects showed classical symptoms for Rett Syndrome with non-inherited genetic postnatal disorder caused by mutations in the MECP2 gene.

For efficacy, the following parameters were measured in the female subjects: Rett Syndrome Behavior Questionare (RSBQ), Clinical Global Impressions (CGI-I), hand behaviors (RSBQ), breathing problems (RSBQ), waking during sleep (RSBQ), and glutamate biomarker, and GABA biomarkers.

Evaluation of the efficacy was measured as a comparison from baseline (week 0), week 4, and to end of treatment (week 7). Blood plasma samples were analyzed at week 0 and at week 7 to measure the levels of glutamate and GABA biomarkers. The evaluation of efficacy used a two-tailed statistical analysis.

The data provided in FIG. 1, FIG. 2 (A through D), and FIG. 3 (A through E) shows a vast improvement of parameters measured with female subjects orally administered a liquid formulation of ANAVEX2-73.

Figure 2A:
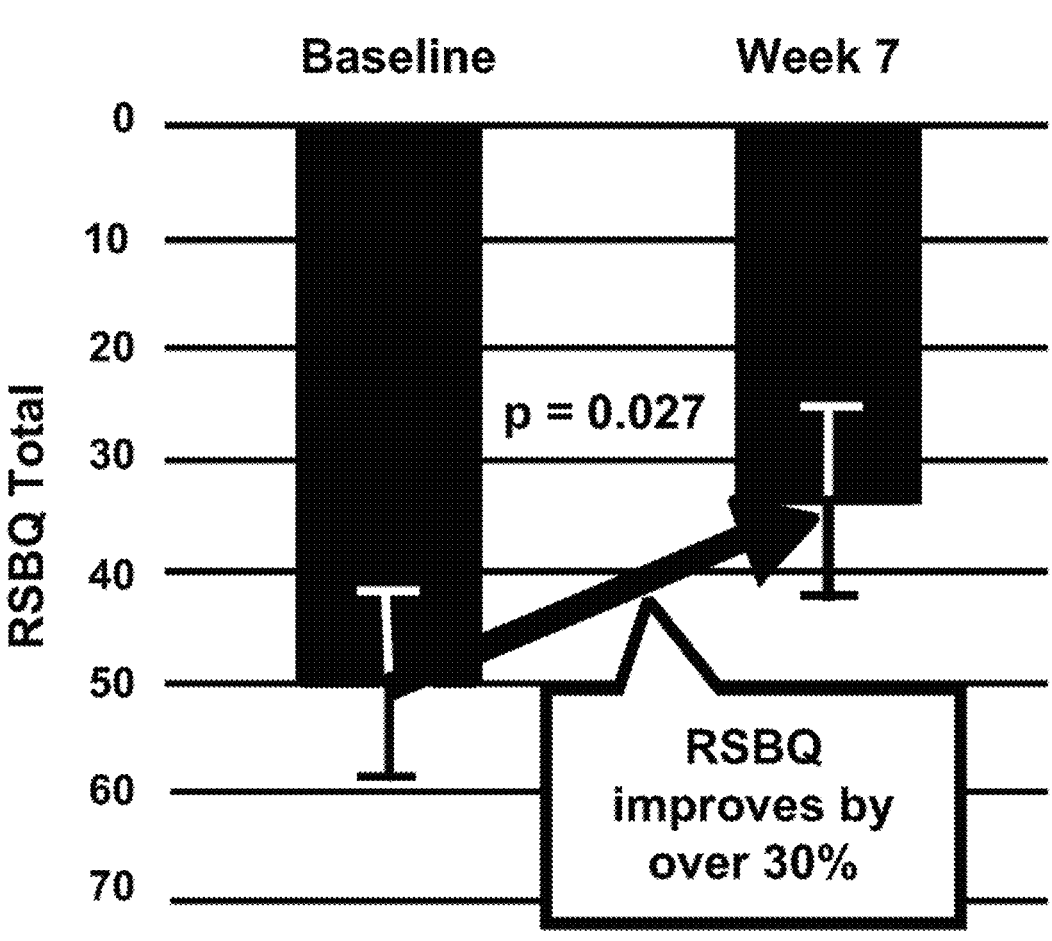
FIG. 2A is a graph of a behavioral index (RSBQ Total Score) over time in 6 young adult female Rett syndrome patients treated daily with 5 mg ANAVEX2-73 in a liquid formulation, from week 0 to end of treatment at week 7.
Figure 2B:
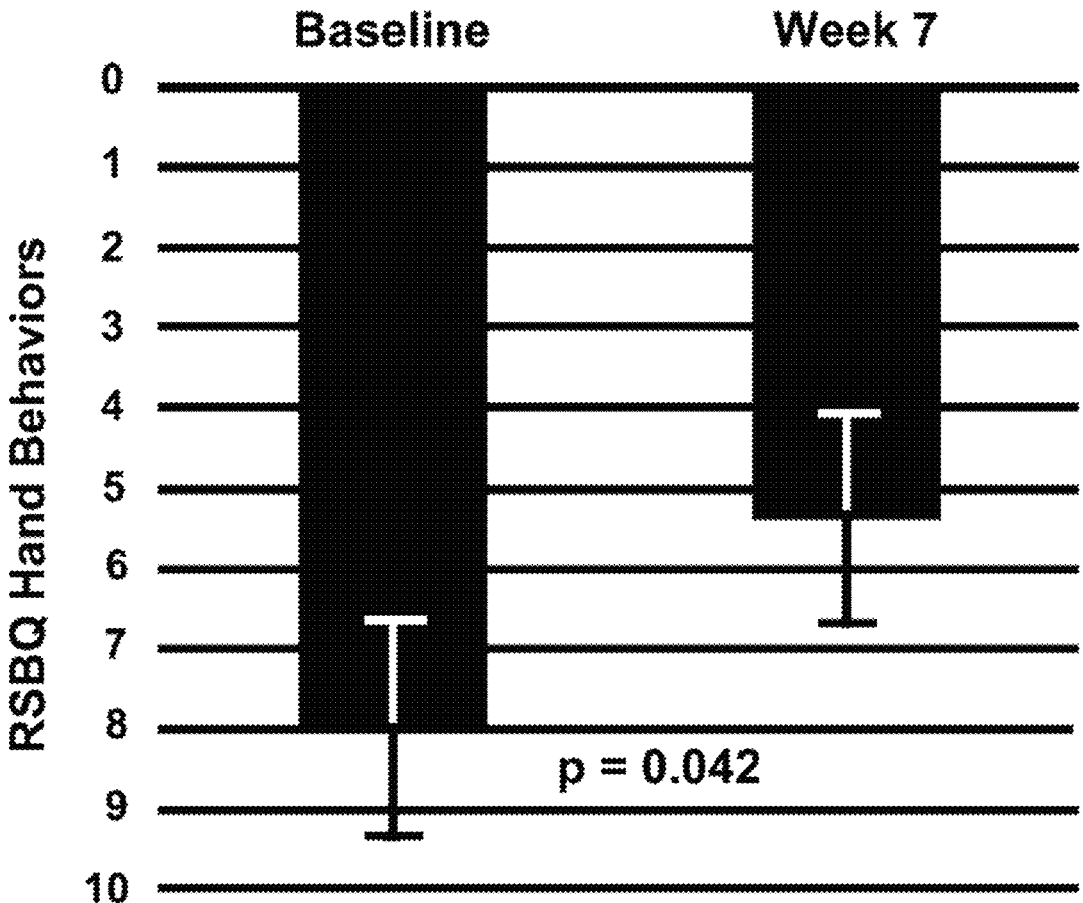
FIG. 2B is a graph of a measurement of hand behaviors (RSBQ) over time in 6 young adult female Rett syndrome patients treated daily with 5 mg ANAVEX2-73 in a liquid formulation, from week 0 to end of treatment at week 7.
Figure 2C:
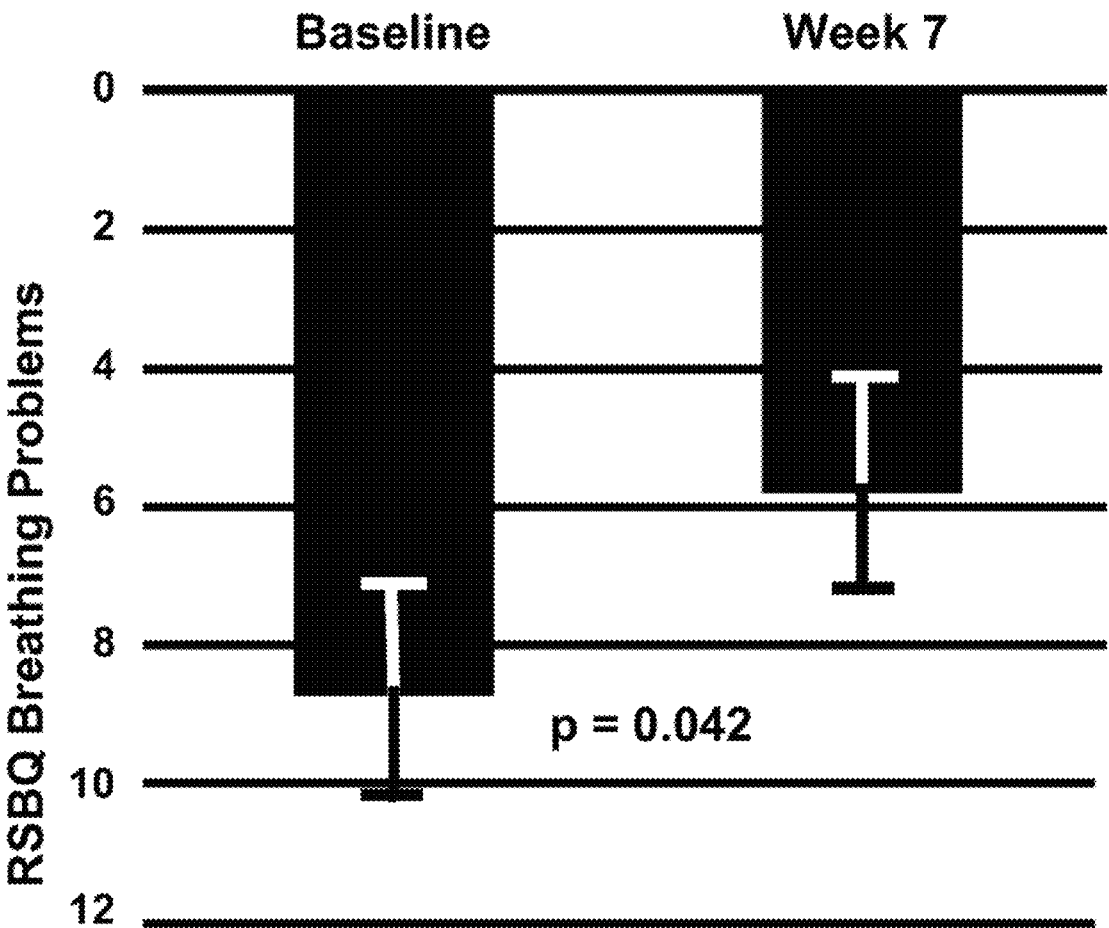
FIG. 2C is a graph of a measurement of breathing problems (RSBQ) over time in 6 young adult female Rett syndrome patients treated daily with 5 mg ANAVEX2-73 in a liquid formulation, from week 0 to end of treatment at week 7.
Figure 2D:
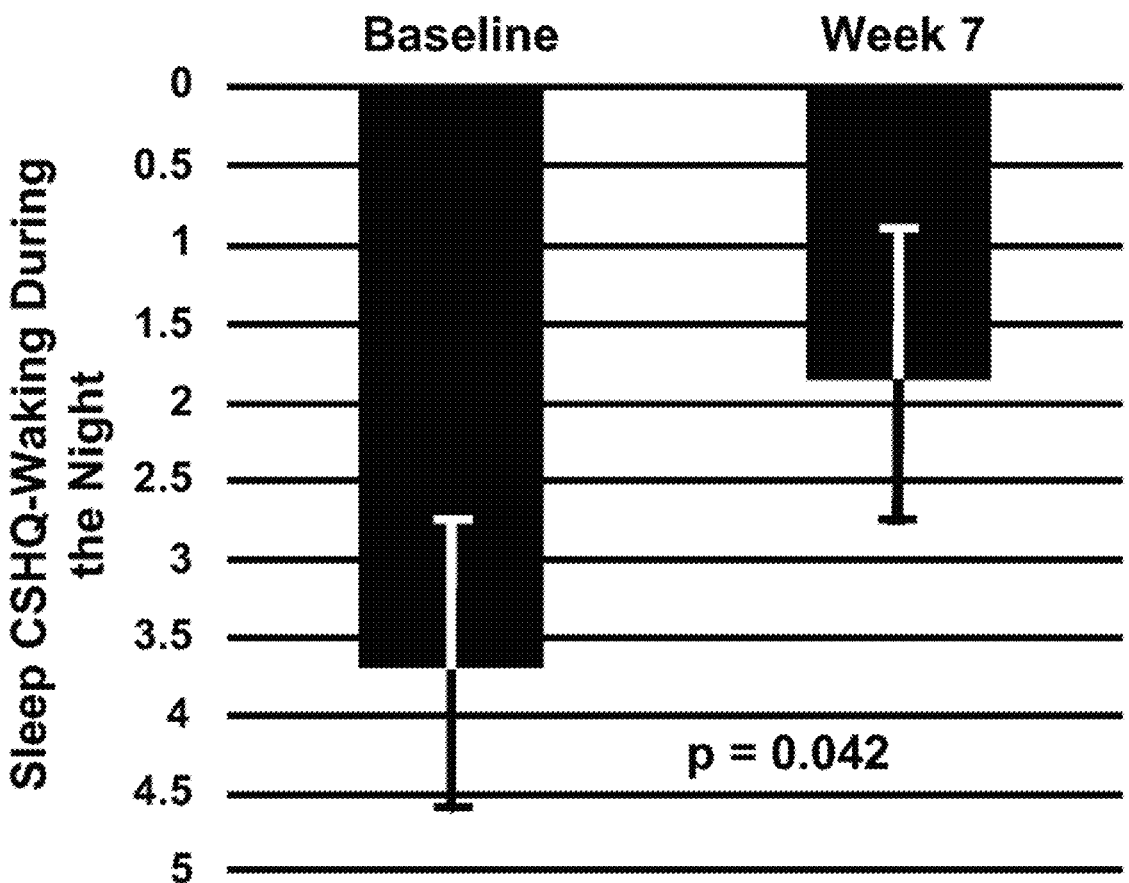
FIG. 2D is a graph of a measurement of waking during sleep (RSBQ) over time in 6 young adult female Rett syndrome patients treated daily with 5 mg ANAVEX2-73 in a liquid formulation, from week 0 to end of treatment at week 7.

As shown in FIG. 1 and FIG. 2A, all six subjects showed improvement in the RSBQ by over 30%. FIGS. 1 and 2A demonstrates a Wilcoxon Signed Ranks Test, RSBQ Total Week vs. Week 7: of $Z=-2.207$ and p (2-tailed)=0.027. For hand behaviors (RSBQ), female subjects showed an improvement as compared to week 0 which was statistically significant (p=0.042) as shown in FIG. 2B. For breathing problems (RSBQ), female subjects showed an improvement as compared to week 0 which was statistically significant (p=0.042) as shown in FIG. 2C. For waking during sleep (RSBQ), female subjects showed an improvement as compared to week 0 which was statistically significant (p=0.042) as shown in FIG. 2D.

Levels of glutamate biomarker in plasma (BIO-MARKER) also decreased significantly (Week 0 vs. Week 7, Wilcoxon Signed Ranks Test: $Z=-1.992$, p (2-tailed) =0.046). Glutamate is the main excitatory neurotransmitter in the brain and is known to be increased in brain (magnetic resonance spectroscopy), CSF, and plasma in Rett syndrome.

Figure 3A:
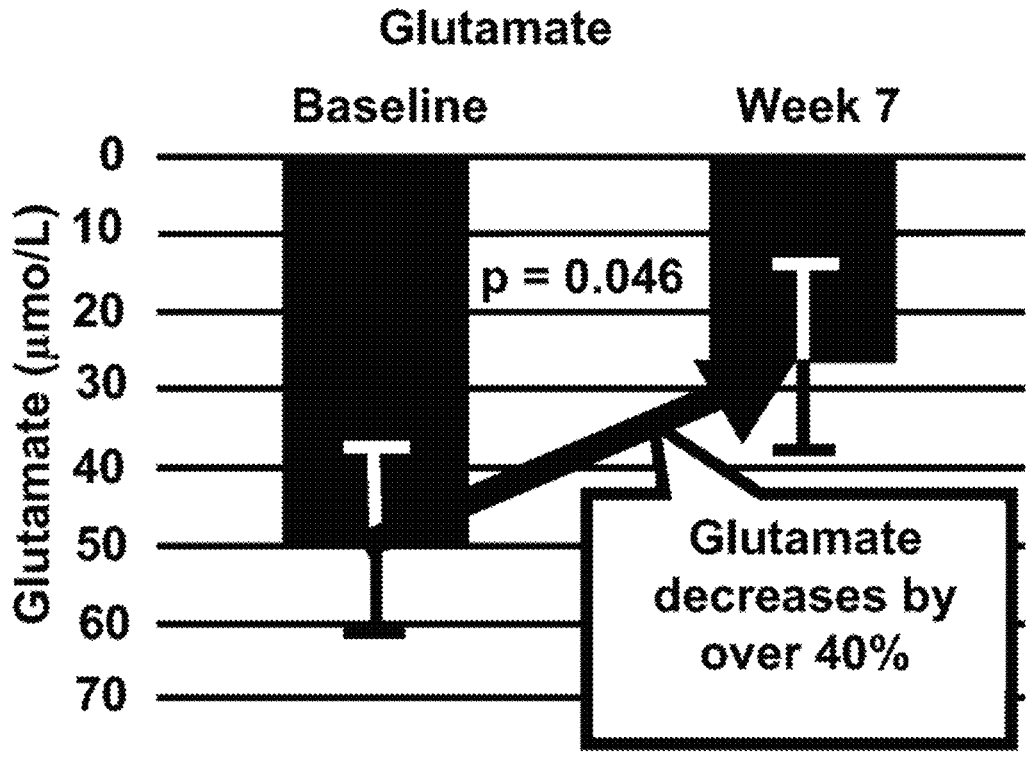
FIG. 3A is a graph of plasma glutamate levels over time in 6 young adult female Rett syndrome patients treated daily with 5 mg ANAVEX2-73 in a liquid formulation, from week 0 to end of treatment at week 7.
Figure 3B:
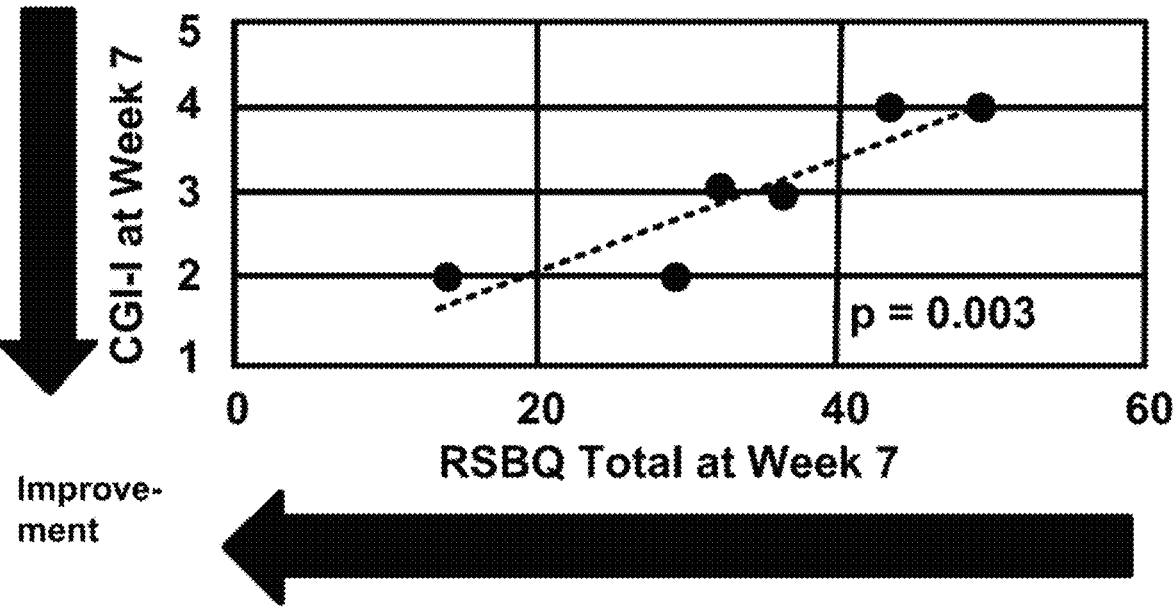
FIG. 3B is a graph correlating RSBQ and CGI-I over time in 6 young adult female Rett syndrome patients treated daily with 5 mg ANAVEX2-73 in a liquid formulation, from week 0 to end of treatment at week 7.
Figure 3C:
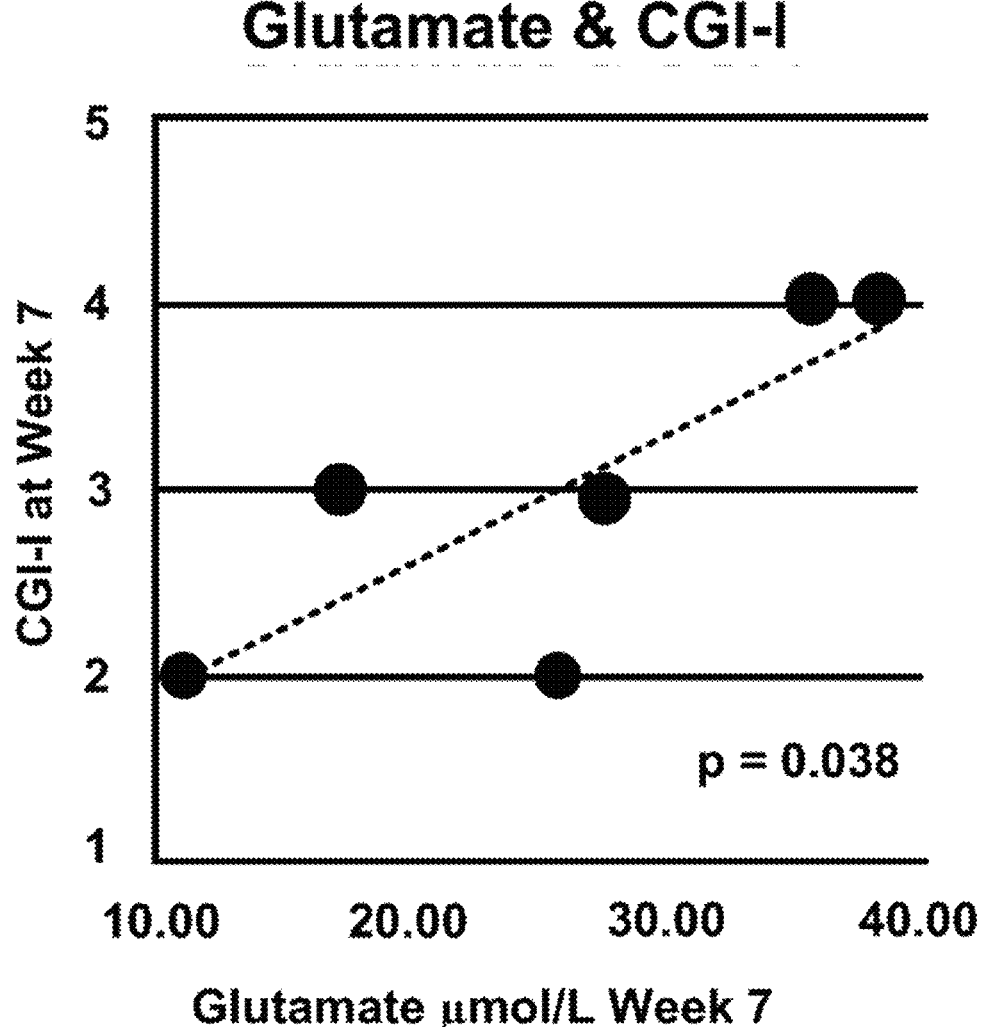
FIG. 3C is a graph correlating plasma glutamate levels and CGI-I over time in 6 young adult female Rett syndrome patients treated daily with 5 mg ANAVEX2-73 in a liquid formulation, from week 0 to end of treatment at week 7.
Figure 3D:
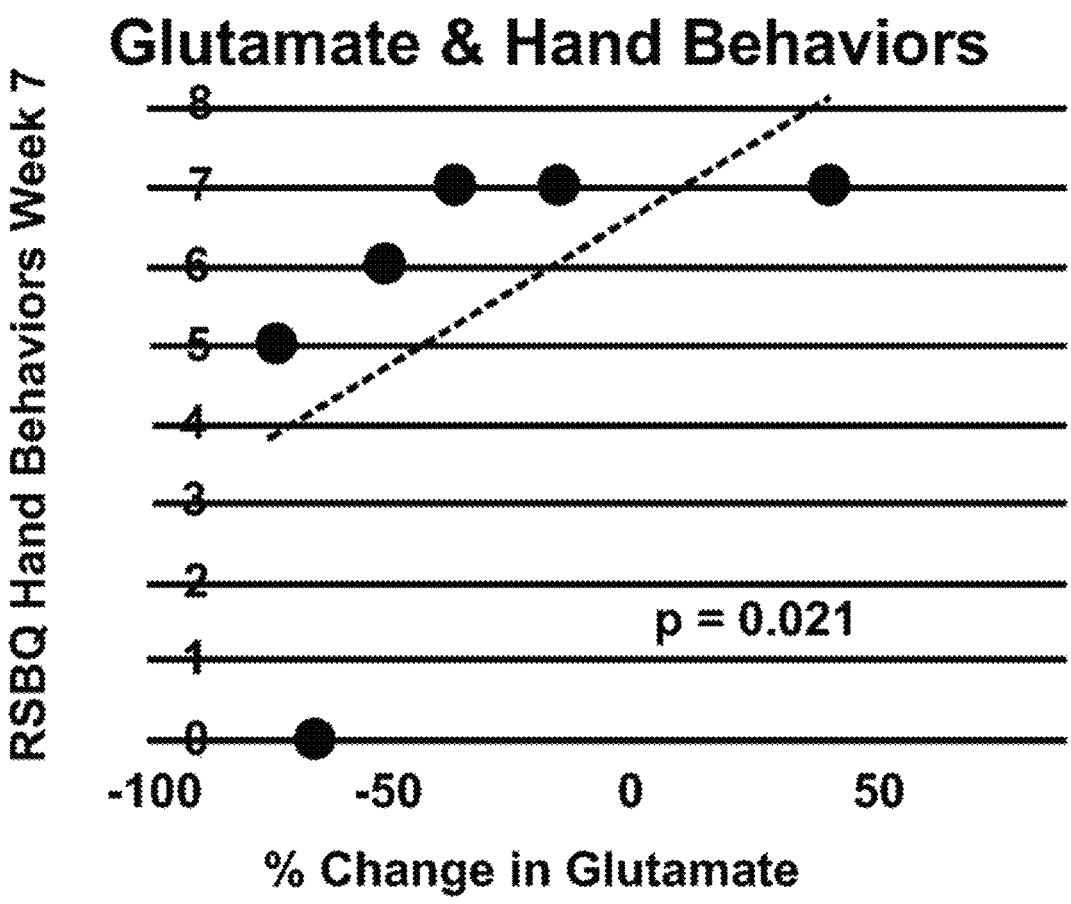
FIG. 3D is a graph correlating plasma glutamate levels and hand behaviors (RSBQ) over time in 6 young adult female Rett syndrome patients treated daily with 5 mg ANAVEX2-73 in a liquid formulation, from week 0 to end of treatment at week 7.
Figure 3E:
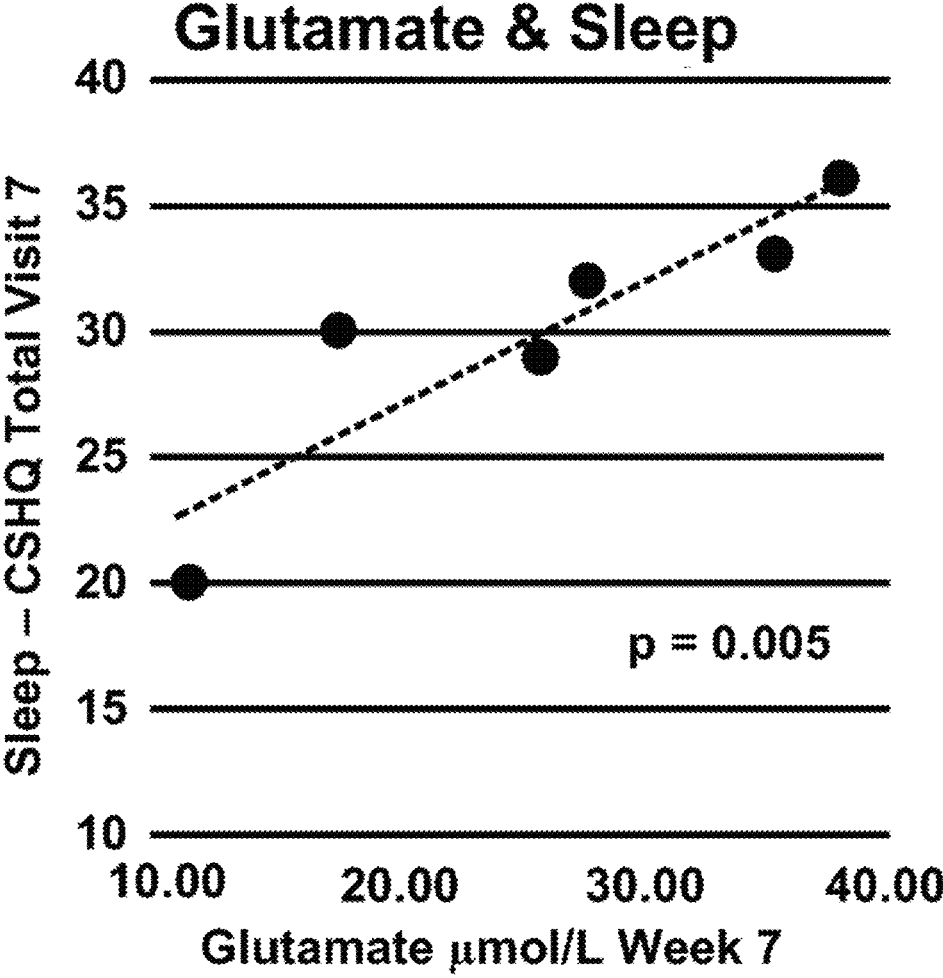
FIG. 3E is a graph correlating plasma glutamate levels and waking during sleep (RSBQ) over time in 6 young adult female Rett syndrome patients treated daily with 5 mg ANAVEX2-73 in a liquid formulation, from week 0 to end of treatment at week 7.

Levels of glutamate at the end-of-treatment (Week 7) were directly correlated with CGI-I scores at the end-of-treatment (Spearman pairwise: rho=0.837, p (2-tailed) =0.038). In addition, the magnitude of decrease in glutamate was inversely correlated with both RSBQ (Spearman pairwise: rho=0.886, p (2-tailed)=0.019) and CGI-I (Spearman pairwise: rho=0.837, p (2-tailed)=0.038) scores, with greater decreases in glutamate associated with lower scores at the end-of-treatment. A graph showing the levels of glutamate biomarker at week 7 directly correlated with CGI-I scores at week 7 is shown in FIG. 3C. There was a significant correlation between RSBQ and CGI-I during the study. An improvement showed a reduction in RSBQ and CGI-I after 7 weeks which was statistically significant (p=0.003) as shown in FIG. 43. Greater decreases in glutamate associated with greater improvement in hand behaviors and sleep behaviors as shown in FIGS. 3D and 3E. Each of these correlation were statistically significant (for FIG. 3D, p=0.021 and for FIG. 3E, p=0.005). For the GABA biomarkers, GABA changes demonstrated an inverse correlation of the magnitude of glutamate changes (2-tailed Spearman's rho=−0.829, p=0.042).

Example 6: ANAVEX2-73 for Rett Syndrome

A female subject, age 5, diagnosed with Rett Syndrome is administered 1 mL of a liquid formulation (0.2 mg/mL). The subject shows improvement in the CGI-I index and the Rett Syndrome Behavior Questionnaire (RSBQ).

Example 7: ANAVEX2-73 for Fragile X Syndrome (FXS)

Fragile X Syndrome (FXS), the most common inherited neurodevelopmental disorder, results from an expansion (full mutation) of a CGG repeat in the 5' untranslated region of FMR1 on the X chromosome that leads to gene silencing and deficit in the fragile X mental retardation protein (FMRP) (Hagerman et al., 2009). FMRP plays a critical role in synaptic development and function (Bagni & Zukin, 2019) and its deficiency is associated to abnormalities in virtually all major brain signaling pathways, among them Adenylate cyclase/Protein Kinase A (PKA) (Berry-Kravis et al., 1995; Sears et al., 2019), Phosphatidylinositol 3-kinase/ Protein Kinase B/mechanistic target of rapamycin (PI3K/ Akt/mTOR) (Sharma et al., 2010; Hoeffer et al., 2012), mitogen-activated protein kinase/extracellular signal-regulated kinase (MAPK/ERK) (Weng et al., 2008; Sawicka et al., 2016), and glycogen synthase kinase 3 (GSK-3□□) (Hagerman et al., 2009). Linking these multiple signaling and synaptic processes is brain-derived neurotropic factor (BDNF), which interacts bidirectionally with FMRP (Casten & Casten, 2014), and may be important for compensating both signaling and synaptic abnormalities.

Recently it was reported that administration of ANAVEX2-73 to a murine model of FXS (Fmr1 knockout 2 mice, KO2) led to marked improvement or normalization in three neurobehavioral phenotypes of clinical relevance (open field test, contextual fear conditioning, marble-burying). The drug also normalized BDNF levels in the hippocampus, see details in Reyes et al. (*Scientific Reports* (2021) 11:17150), which is incorporated herein by reference in its entity. Testing of ANAVEX2-73 was conducted because of its therapeutic potential in FXS and other neurologic disorders like Rett syndrome, and neurodegenerative disorders including Alzheimer's disease and Parkinson's disease considering S1R's role in calcium homeostasis and mitochondrial function, both critical for synaptic function, and early work with ANAVEX2-73 and other S1R agonists supporting their positive effect on synaptic abnormalities and neurobehavioral impairments.

In the aforementioned study by Reyes et al., ANAVEX2-73 or saline were administered twice daily at a dose of 1 mg/kg IP, to 2-month-old Fmr1 KO2 mice and wild type counterparts (N=10 mice per group, 40 mice total; for blood sample analyses: 5-7 mice per group) for two weeks. Brain samples were harvested for biochemical and molecular studies, blood samples were collected at baseline and on the last day of the behavioral assessments. Complementary cell signaling analyses were also conducted. These analyses were important because of their relevance to both preclinical and clinical research in FXS. Peripheral lymphocytes were isolated and stimulated with Phorbol-12-Myristate-13-Acetate in a buffer without phosphatase inhibitors but with U0126 (inhibitor of MAPK kinase). Cells were permeabilized by addition of cold methanol for 30 min, washed twice in PBS with 2% FACS wash buffer (FBS), fixed, and stained with Alexafluor488-labeled monoclonal antibodies to phosphorylated (activated) Akt (pAkt) and ERK (pERK) (BD Biosciences, Franklin Lakes, NJ) in the dark for 30 min, followed by two washes in FBS. Resuspended cells were analyzed in a Coulter XL3 flow cytometer. Flow cytometry was also employed to confirm lymphocyte identity by staining with an anti-CD3 (T cell receptor) antibody. Levels of pAkt and pERK were first characterized in terms of distribution, by the Shapiro-Wilk test of normality and Levene's and Bartlett's tests, which determined that all data were distributed normally and had equal variances. The first group of analyses aimed at identifying ANAVEX2-73's efficacy by comparing drug-treated with vehicle-treated Fmr1 KO2 groups on each molecular assay by the Student's t-test. Once a significant difference was found, a two-way univariate ANOVA with genotype and treatment as between-subject factors, followed by a Tukey's post-hoc test, evaluated the differences between drug-treated and vehicle-treated WT and Fmr1 KO2 mice. These analyses intended also to confirm that the molecular phenotype of vehicle treated Fmr1 KO2 was abnormal. Analyses were conducted using SPSS version 25 (IBM, Armonk, NY, USA), as well as several online calculators including Statistics Kingdom, Statology, and iCalcu.com.

Figure 4A:
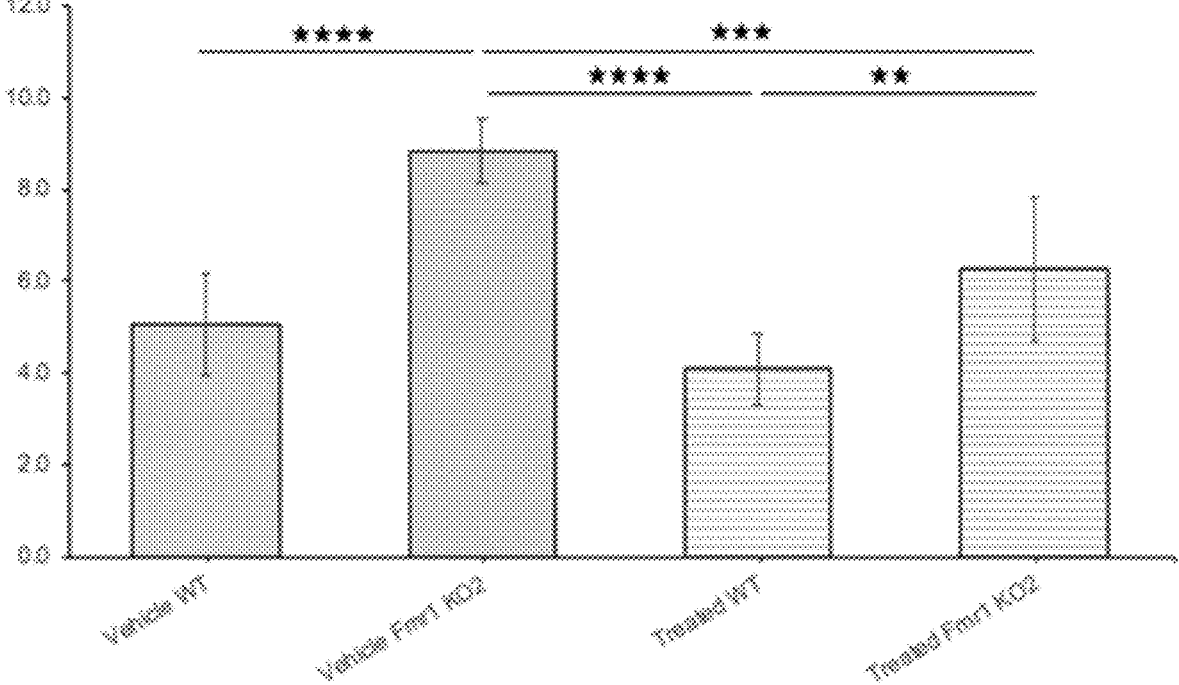
FIG. 4A is pAkt levels in peripheral lymphocytes in Fmr1 KO2 mice vs wild type (WT) mice, ANAVEX2-73 treated or saline vehicle treated (N=5 per group). P value indicators: ** for p<0.001; * for p=0.01; ** for p<0.05; other comparisons not significant.
Figure 4B:
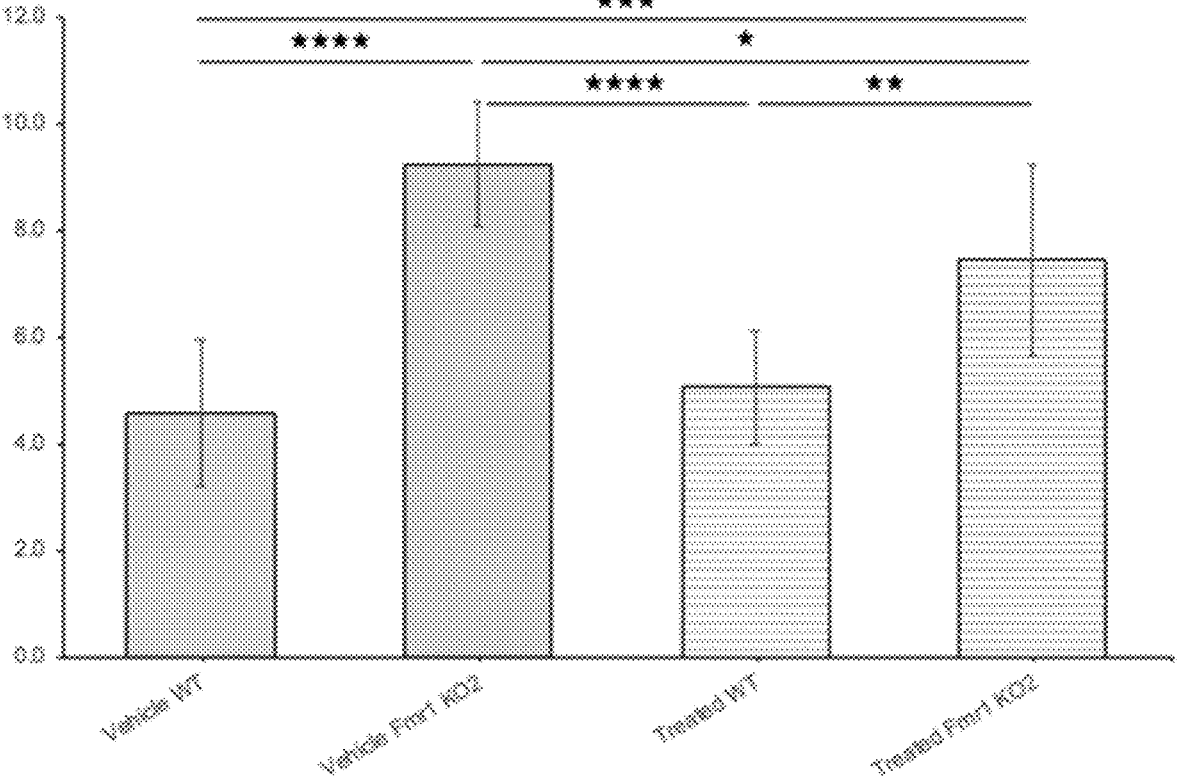
FIG. 4B is pERK levels in peripheral lymphocytes in Fmr1 KO2 mice vs wild type (WT) mice, ANAVEX2-73 treated or saline vehicle treated (N=7 per group). P value indicators: ** for p<0.001; * for p=0.01; ** for p<0.05; other comparisons not significant.

Analyses of the effects of ANAVEX2-73 on pAkt, by comparing vehicle- and drug-treated Fmr1 KO2 mice, performed on groups of 5 animals each showed significantly lower pAkt levels in ANAVEX2-73-treated animals ($p=0.01$). ANOVA confirmed the elevation in pAkt in vehicle-treated Fmr1 KO2 mice; it also demonstrated its correction after ANAVEX2-73 administration with pAkt levels in drug-treated mutant mice comparable to those in vehicle-treated WT mice (FIG. 4A). The results showed that reatment with ANAVEX2-73 normalized elevated levels of pAkt in lymphocytes of Fmr1 KO2 mice (Fmr1 K02-Vehicle vs. WT-Vehicle, Fmr1 K02-Vehicle vs. WT-Treated: Both **$p<0.001$; Fmr1 K02-Vehicle vs. Fmr1 K02-Treated *$p=0.01$; Fmr1 K02-Treated vs. WT-Treated **$p<0.05$; other comparisons not significant).

pERK levels displayed a similar profile to those of pAkt, although the differences between drug- and vehicle-treated Fmr1 KO2 mice were borderline significant (Student's t-test $p=0.046$). The ANOVA, which was based on 7 animals per group, also showed the marked increase in pERK levels in Fmr1 KO2 mice when vehicle-treated mutant animals were compared to their WT counterparts ($p<0.001$). Posthoc tests demonstrated mild reductions in pERK in drug-treated Fmr1 KO2 mice (versus vehicle-treated Fmr1 KO2 mice: $p=0.096$) (FIG. 2). The results showed that treatment with ANAVEX2-73 mildly reduced elevated levels of pERK in lymphocytes of Fmr1 KO2 mice (N=7 per group; Fmr1 K02-Vehicle vs. Fmr1 K02-Treated *$p=0.05-0.10$; Fmr1 K02-Vehicle vs. WT-Vehicle, Fmr1 K02-Vehicle vs. WT-Treated: Both **$p<0.001$; Fmr1 K02-Treated vs. WT-Vehicle *$p<0.01$; Fmr1 K02-Treated vs. WT-Treated **$p<0.05$; other comparisons not significant).

Analysis of blood samples from Fmr1 KO2 mice confirmed the abnormal activation of the PI3K/Akt/mTOR and MAPK/ERK signaling pathways previously reported in brains from murine models of FXS as well as in lymphocytes from affected individuals. As recently communicated by Reyes et al., ANAVEX2-73, a S1R agonist, corrects several molecular and behavioral phenotypes in Fmr1 KO2 mice. The data here demonstrated that key FXS signaling abnormalities in lymphocytes were also improved by administration of ANAVEX2-73. Thus, peripheral cell signaling improvements were temporally correlated with positive effects on brain signaling (i.e., BDNF) and behavior. These data had several implications. First, abnormalities in key signaling pathways involved in FXS pathogenesis can be monitored in peripheral cells, such as lymphocytes, both in mouse models and affected individuals. Second, characterization of mouse models of FXS and testing of potential treatments in these animals should ideally include blood sample analyses. In terms of the drug under study, these data supported the evaluation of cell signaling in blood samples of animal models of other neurologic disorders that could benefit from treatment with ANAVEX2-73. Likewise, clinical studies of ANAVEX2-73 and related compounds should consider the inclusion of lymphocyte cell signaling assays among their biomarkers. Whether the observed greater effect on pAkt than on pERK reflects a relative selectivity of S1R agonists deserves further examination. Nevertheless, the role of the Akt/mTOR pathway in regulating neuronal autophagy and the recent demonstration that ANAVEX2-73 enhanced autophagy in both animal and cellular supported such specificity. In summary, evaluations of lymphocyte cell signaling in mouse models of FXS were feasible and supported corresponding assessments in affected individuals. These analyses had the potential for monitoring response to treatment, particularly for drugs correcting multiple pathway abnormalities such as S1R agonists. Implications of this work extended beyond FXS to most neurologic disorders associated with abnormal cell signaling.

What is claimed is:

1. A method for treating Fragile X Syndrome in a subject in need thereof, the method comprising:

(a) evaluating the subject for the occurrence and/or severity of one or more Fragile X Syndrome symptoms selected from the group consisting of: cognitive impairment, motor learning impairment, balance impairment, muscular strength impairment, seizures, sleep dysfunction, breathing impairment, and anxiety;

(b) measuring a baseline level of at least one biomarker in the subject to determine a baseline biomarker level, wherein the biomarker is selected from plasma glutamate, PI3K, pAkt, mTOR, pMAPK, pERK, and any combination thereof;

(c) daily administering to the subject a dosage formulation comprising a therapeutically effective amount of tetrahydro-N, N-dimethyl-2,2-diphenyl-3-furanmethanamine hydrochloride (ANAVEX2-73) for a period of at least about 1 week, wherein the dosage formulation is selected from a liquid oral dosage formulation, a topical formulation, a transmucosal formulation, a transdermal formulation, a buccal formulation, a sublingual formulation, and a parental formulation;

(d) re-evaluating the subject for the occurrence and/or severity of the symptoms evaluated in (a), evaluating the subject for the occurrence of adverse events; and measuring the biomarker level in the subject to determine a second biomarker level and comparing the second biomarker level to the baseline biomarker level; and (e) optionally modifying the dosage of ANAVEX2-73 administered to the subject based on the re-evaluations in (d) and the second biomarker level in (d), wherein absence of improvement in at least one symptom indicates optionally increasing the dosage of ANAVEX2-73, occurrence of an adverse event indicates decreasing the dosage of ANAVEX2-73, and the second biomarker level about the same or higher than the baseline biomarker level indicates optionally increasing the dosage of ANAVEX2-73.

2. The method of claim 1, wherein the amount of ANAVEX2-73 is from about 0.2 mg to about 40 mg.

3. The method of claim 1, wherein the dosage formulation comprises ANAVEX2-73 at a concentration of about 0.2 mg/ml to about 8 mg/ml.

4. The method of claim 1, wherein the dosage formulation is a liquid oral dosage formulation comprising about 0.2 mg to about 40 mg of ANAVEX2-73, and at least one of a preservative and a flavoring agent.

5. The method of claim 1, wherein the therapeutically effective amount of ANAVEX2-73 is administered in at least one dose of the liquid dosage formulation, at least once daily.

6. The method of claim 1, wherein the at least one biomarker is selected from pAKt and pERK.

7. The method of claim 6, wherein at least two biomarkers are selected, and the at least two biomarkers are pAKt and pERK.

* * * * *